United States Patent [19]

Voges et al.

[11] 4,405,163

[45] Sep. 20, 1983

[54] COUPLING FOR MEDICAL APPARATUS TUBES

[75] Inventors: Karl-Friedrich Voges; Claus Haacke, both of Melsungen; Peter Heise, Fuldabrück, all of Fed. Rep. of Germany

[73] Assignee: Intermedicat GmbH, Emmenbrucke, Switzerland

[21] Appl. No.: 209,744

[22] Filed: Nov. 24, 1980

[30] Foreign Application Priority Data

Dec. 12, 1979 [DE] Fed. Rep. of Germany ....... 2949865

[51] Int. Cl.³ .............................................. F16L 37/08
[52] U.S. Cl. ..................................... 285/305; 285/315; 285/322; 285/332; 285/DIG. 7; 285/320; 604/283; 604/905
[58] Field of Search ......... 285/255, 243, 322, DIG. 7, 285/323, 316, 315, 320, 305, 332; 604/93, 905, 408, 283; 128/207.14

[56] References Cited

U.S. PATENT DOCUMENTS

| | | | |
|---|---|---|---|
| 1,043,683 | 11/1912 | Fieser | 285/243 |
| 1,104,955 | 7/1914 | Bellows | 285/320 |
| 1,113,080 | 10/1914 | Wilson | 285/243 |
| 2,446,599 | 8/1948 | Knaggs | 285/243 |
| 2,675,829 | 4/1954 | Livers | 285/322 X |
| 2,868,564 | 1/1959 | Arras | 285/243 |
| 3,394,950 | 7/1968 | Jensen | 285/322 X |
| 3,724,882 | 4/1973 | Dehar | 285/243 |
| 3,918,679 | 11/1975 | Silvana | 285/316 X |
| 4,068,870 | 1/1978 | Whitney et al. | 285/320 |
| 4,108,475 | 8/1978 | Fleischer | 285/320 X |

Primary Examiner—Dave W. Arola
Attorney, Agent, or Firm—Merriam, Marshall & Bicknell

[57] ABSTRACT

A coupling for connecting the ends of medical apparatus tubes. The coupling has male and female conical mating elements on first and second end pieces. Each end piece is adapted to receive the end of a tube. The end pieces are locked together to prevent unintentional separation. Locking is achieved by at least one finger extending from one end piece to the other end piece. The finger, in addition to its locking function, resists tension when tensile stress is applied to a coupled tube.

10 Claims, 9 Drawing Figures

COUPLING FOR MEDICAL APPARATUS TUBES

This invention relates to couplings. More particularly, this invention is concerned with a coupling for joining together the ends of two tubes, particularly tubes used in medical apparatus or for medical purposes.

BACKGROUND OF THE INVENTION

Previously, the tubes of catheters and similar devices have been connected to other tubes by the use of two end pieces. One end piece was rigid and the other was flexible. The flexible end piece generally contained a female conical bore or hole while the other, or male, end piece had an outer conical shape which could be pressed into the conical bore. Since these types of tube couplings were not standard, the diameters, lengths and conical angles or tapers varied from manufacturer to manufacturer. Nevertheless, due to the elasticity of the flexible female conical member, end pieces with various different dimensions could be used. There was, however, a substantial danger with such connections that they would unintentionally separate.

It is of particular importance for safety that accidental disconnection of joined tubes not take place when bladder catheters are used in urine collecting systems. Because of tension applied to tubes by restless and careless patients, unintended separation of the tube connection occurs, urine leaks out and the connection is contaminated with bacteria. Investigations have established that contamination of the connection location is a main cause of urinary duct infections. Therefore, because of the great danger of contamination, the hose connection should not be separable or disconnectable, not even by the nursing personnel. A need accordingly exists for a tube coupling for medicinal purposes where unintended disconnection, even under severe tension or pulling, is prevented.

SUMMARY OF THE INVENTION

According to the present invention, there is provided a tube coupling having first and second end pieces which nest together in a liquid tight joint, a longitudinal finger mounted to one end piece, and means for engaging the finger in locking arrangement with the other end piece.

Since the finger is mounted to one end piece and it also engages the other end piece, the two end pieces cannot be pulled apart because they are bridged or spanned by the finger and are thereby secured together relative to one another. As a result of this bridging, it is also possible to use end pieces having cone measurements which deviate from one another without there being a danger of separation under tension. Furthermore, because of the bridging finger, the connecting area at which the conical members mate or nest, is relieved from tensile stress.

The coupling provided by this invention is particularly suitable for the connection of bladder catheters with urine collecting systems. This is because the danger of infection is especially great if a loose tube connection occurs in such systems. A high degree of safety and secure sealing is needed for tube connections used in such system. Those needs are met by the coupling provided by this invention.

The second end piece desirably has a mounting, at its inner or rearward end, to which the finger is connected. This simple type of support or mounting for the finger evenly distribute tensile forces, transferred by the finger, from the first end piece to the second end piece.

In a preferred embodiment of the invention, the mounting constitutes a ring which is supported by the inner or rearward end or shoulder of the second end piece. This ring support can be a radial flange. A plurality of fingers project axially from the ring and these fingers can be made of increasing thickness, and thus increasing strength, as the distance from the ring increases. The ring supporting the fingers is desirably surrounded by a slidable ring which can be slid on and over the fingers. The slidable ring thereby presses the fingers ever more tightly against the first end piece. The described clamping action can be increased by making the first end piece outer surface conical and with the widest part of the cone being at the outer end of the first end piece. Preferably, the fingers are evenly distributed or spaced axially around the circumference of the second end piece so that tensile stresses are distributed circumferentially.

If it is considered desirable to avoid the application of substantial radial pressure by the locking fingers then, according to another embodiment of coupling provided by the invention, the plurality of pivotal fingers can be provided at their outer or forward ends with one or more inwardly directed steps which are adapted to engage the inner end of the first end piece. When the slidable ring is slid over such fingers, the fingers do not apply radial pressure on the first end piece. The slidable ring is moved readily in either direction to lock and unlock the fingers.

As mentioned above, in some situations it is necessary to couple hoses in a manner which prevents their disconnection by nursing personnel. To meet this requirement, a further variation of the invention is provided in which the outer surface of the fingers is made sawtooth or serrated. If desired, the fingers can increase in thickness towards their free ends. When the slidable ring is slid along the surface of the fingers, it consecutively engages the teeth or serrations on the fingers. As a result, under normal circumstances it is not possible to move the slidable ring backwards to release the fingers. The sawtooth fingers, together with the ring, for a kind of ratchet which permits movement of the slidable ring in only one direction.

Locking of the coupling does not necessarily have to be accomplished by axial movement of a slidable ring. In further embodiments of the invention, coupling locking can be achieved by pressing two opposing parts together into clamping engagement. Thus, two fingers positioned opposite each other are provided with cooperating complementary locking elements which, in the engaging arrangement, tightly surround and clamp onto the conical outer area of the first end piece. It is important that the locking elements, which are brought into engagement by opposing radial displacement, cannot move apart or separate unintentionally. To prevent unintentional separation, the locking elements can have complementary or cooperating serrations. Alternatively, the locking elements can have pin and hole structures which engage tightly by a press fit. For this purpose, the pins can be made slightly larger than the holes.

According to a further variation of the invention, the locking means comprises an annular, or partially annular, member which engages the conical outer surface of the first end piece, and a finger extending axially from the annular member adapted to engage with a locking means on a mounting on the second end piece. This embodiment can be manufactured relatively inexpensively. The locking means, for example, can be either serrations or teeth, or perforations. The annular piece is desirably shaped like a C and is adapted to only partially surround the first end piece in a resilient or elastic manner.

An advantage of the tube couplings provided by the invention is that, upon slight axial movement of the first and second end pieces due to the application of a tensile stress, the locking means engaging the first end piece is tightened even more so that its support strength and clamping force are increased automatically. Accordingly, the locking means does not have to be tightened initially to its maximum stress capacity since, in the case of stress, tightening occurs inherently up to the necessary requirements. The tensile strength of the tube is determined exclusively by the strength of the material used in its production and not by the coupling. Futhermore, the application of tension on the tube cannot separate the coupling without its being destroyed.

DETAILED DESCRIPTION OF THE DRAWINGS

To the extent it is practical and convenient, the same numbers will be used to identify the same or similar parts or elements in the various views of the drawings.

Figure 1:
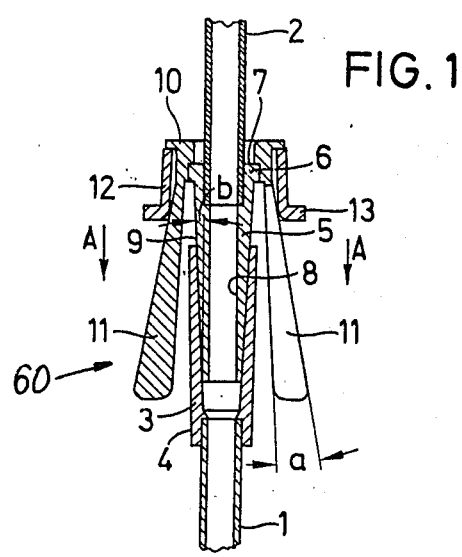
FIG. 1 is a longitudinal sectional view through a preferred embodiment of coupling, for joining two tube ends, having a slidable ring which locks clamping fingers against mating or nesting conical members.

The embodiment of the invention illustrated by FIG. 1 shows the ends of two tubes 1 and 2 connected or joined together by means of a tube coupling 60 provided by the invention. The coupling 60 has a short tubular first end piece 3 which is adapted to receive the end of tube 1 at its inner or rear end. The end of tube 1 can be secured in place by plastic welding or an adhesive to form a tight leak proof joint. The other, and outer, end of first end piece 3 contains an axial female conical bore, having a cone angle b as shown in FIG. 1, which tapers outwardly towards the outer end of end piece 3. Furthermore, the cross-sectional area 4 of the end piece 3 increases or enlarges slightly going from the inner end to the outer end.

A second short tubular end piece 5 having cylindrical bore 8 is also part of the coupling 60. The end piece 5 is adapted to be joined at an inner end to the end of tube 2, such as by welding or use of an adhesive. The bore 8 is intended to have the same diameter as the diameter of tube 2. The inner end of end piece 5 has a radial flange 6 which contains a rearward, ring-like shoulder 7. The end piece 5 extends forwardly in a radially inward tapering manner, thereby defining a male conical surface 9 which extends to the outer or forward end of end piece 5 at the cone angle b. The cone angle of the female conical bore in the first end piece 3 is the same as that of the male conical surface 9 on the second end piece 5, thereby permitting the conical members to nest securely together with surface-to-surface contact.

Ring 10 is slid onto flange 6, of the second end piece 5, with the ring abutting the shoulder 7. A plurality of fingers 11 on ring 10 project axially forward and extend partially over the first end piece 3. The fingers, whether two, three or more, are axially distributed evenly spaced apart around the circumference of ring 10. The thickness, and thus the strength, of the tapered fingers increases with increasing distance from ring 10. As a result, the fingers are able to hinge or rotate axially near where they meet the ring 10. The angle a of the finger taper is greater than the cone angle b.

Slidable ring 12 is located coaxially on, and initially around, ring 10. Slidable ring 12 has a flange 13 at its front end for reinforcement and as an aid for sliding the ring by hand action. When the slidable ring 12 is moved axially in the direction of the arrows A—A shown in FIG. 1 then, according to the principle of an inclined plane, with a slight force in the direction of the arrows a large radial force is generated. This results in the fingers 11 being clamped firmly between the first end piece 3 and the slide ring 12. A relief or releasable connection is thereby created between the first end piece 3 via the fingers 11, which are clamped to it, and the ring 10 on the second end piece. Tensile stress between the two conical nesting elements is avoided by the clamping action of the fingers. To release the connection, slide ring 12 is slid back axially, such as to the position shown in FIG. 1. The nesting conical members can then be separated to disconnect the ends of tubes 1 and 2.

Figure 2:
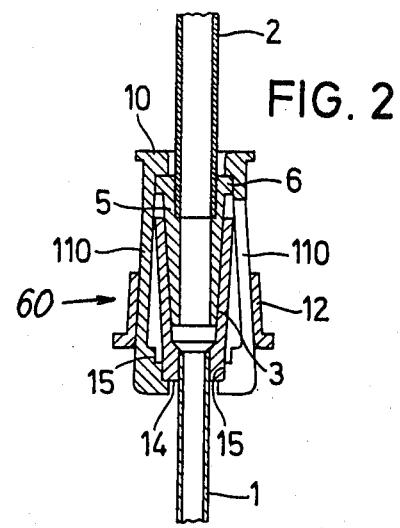
FIG. 2 is similar to FIG. 1 but shows fingers which lock by engaging the inner or rear end of one part of the coupling.

FIG. 2 illustrates a second embodiment of coupling provided by the invention. The embodiment of FIG. 2 is substantially identical to the one shown in FIG. 1. An important, if not essential, difference between them is that in the embodiment of FIG. 2, the fingers 110, which do not increase axially in thickness and strength since they are of uniform thickness except at the outer end, grip the inner, or rear, end 14 of the first end piece 3. The hinged or pivotal fingers 110 extend axially and longitudinally, from ring 10, over the first end piece 3. The outer or forward ends of fingers 110 have inwardly directed steps 15, and at least one of the steps 15 on each finger is adapted to engage the inner end 14 of the first end piece 3 when slidable ring 12 is slid axially forward to pivot the fingers inwardly, such as to the position shown in FIG. 2. When slidable ring 12 is slid back over ring 10, the fingers spring pivotally outwardly out of engagement with the first end piece. The tubes 1 and 2 are then disconnected by separating the nesting conical members.

Figure 3:
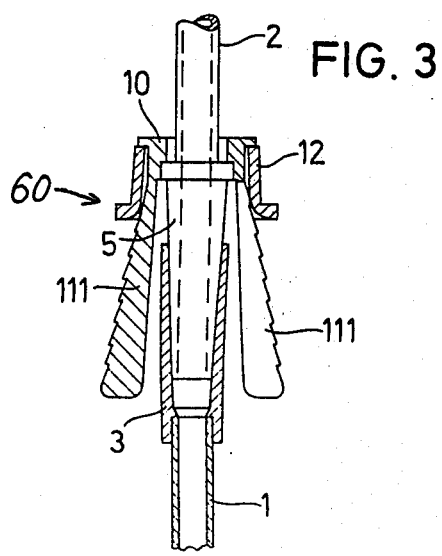
FIG. 3 is similar to FIG. 1 but it shows fingers with serrations which can engage a slidable ring.

The third embodiment, shown in FIG. 3, corresponds largely to the embodiment shown in FIG. 1. The sole difference is that the fingers 111, which become thicker towards their free ends, have a serrated or saw-tooth outer surface. The saw-teeth have depressions or cutout areas with which the rear edge of slidable ring 12 can engage or lock. This structure provides a coupling which is not releasable except with great difficulty since the fingers 111 must all be pushed in radially at one time to provide clearance for ring 12 to be slid back.

Figure 4:
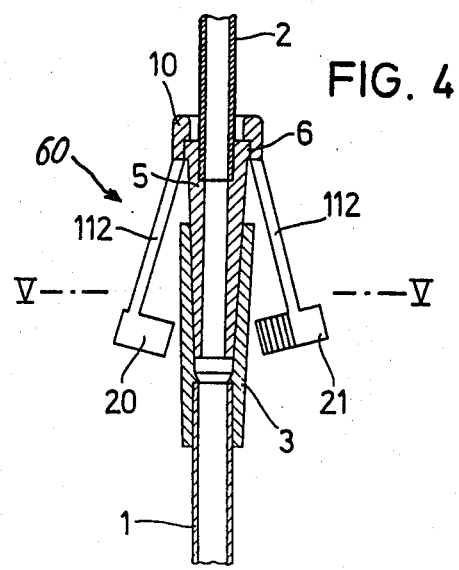
FIG. 4 is a longitudinal sectional view through another embodiment of coupling having fingers with radially locking elements on the ends.
Figure 5:
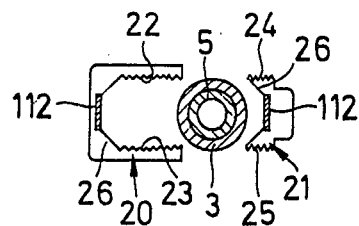
FIG. 5 is a sectional view taken along the line V—V of FIG. 4.

FIGS. 4 and 5 illustrate a fourth, and especially low cost, embodiment of coupling provided by the invention. It is characterized by a locking device which can be manufactured in one-piece from a suitable synthetic polymeric material. As is shown in those figures of the drawings, the locking device has a ring 10 from which two fingers 112 project axially. The ends of the fingers have locking elements 20 and 21. The ring 10, as in the previous embodiments, is supported on a flange 6 on the inner end of the second end piece 5. The first and second end pieces have male-female complementary conical members adapted to engage one another in nesting arrangement when inserted together as shown in FIG. 4.

The shape of the locking elements 20 and 21 is shown by FIGS. 4 and 5 taken together. The locking element 20, on the end of one finger 112, is U-shaped and it has serrations on teeth 22 and 23 on the inner side of each leg of the U-shaped structure. The locking element 21, located on the end of the other and opposite finger 112, has serrations or teeth 24 and 25 on its opposite sides. By finger pressure on locking elements 20 and 21, they are urged towards each other and, as they are so displaced, they surround or envelop the circumference of the first end piece 3. Locking element 21 moves into locking element 20. As a result, the serrations 23 and 25 engage and mesh together, as do the serrations 22 and 24. In this way, the end piece 3 is clamped in between the end piece 5 and the triangular ribs 26 of the locking elements 20 and 21. Since the outer circumference of the first end piece 3 increases towards the outer end, it is not possible, within reason, to axially pull off the locking elements 20 and 21, once they are tightly pressed together, from the end piece 3.

Figure 6:
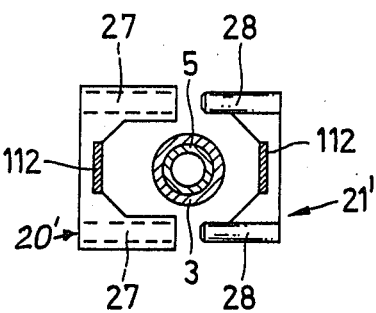
FIG. 6 is similar to FIG. 5 but shows another locking structure using pegs that go into holes with a force fit to form a clamping unit.
Figure 8:
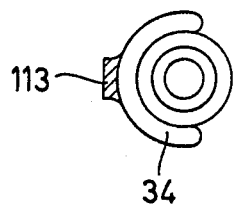
FIG. 8 is an end view of the coupling shown in FIG. 7 taken along the line of arrow VIII.

Another embodiment of the invention is shown in FIG. 6. The locking elements 20' and 21', on the ends of two fingers 112, form a forced-fit clamp. The locking element 20' has two parallel holes 27 into which the pegs 28 of locking element 21' can be forced with a tight fit. The diameters of the pegs 28 are slightly larger than the diameters of holes 27 so that, after they are pressed together, they are secured in locked relationship relative to each other.

Figure 7:
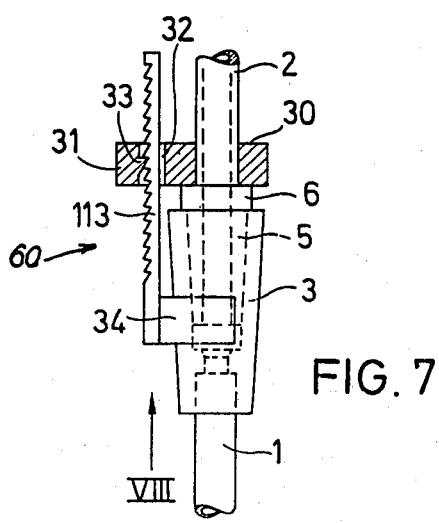
FIG. 7 is an elevational view, partially in section, illustrating a coupling having a toothed or serrated finger which engages a tang to lock the coupling together.

The embodiment of FIG. 7 shows a coupling 60 having the end of tube 1 firmly connected to the first end piece 3 and the end of tube 2 connected to the second end piece 5. The first end piece 3 has a female conical bore and the second end piece 5 has a male conical member which is adapted to nest in surface-to-surface contact with the female conical bore. Ring 30 abuts the inner end of the second end piece 6 and tube 2 extends through it from the rear. Ring 10 has a lateral projection 31 which has an opening 32 in which a tang or tooth 33 is located. A finger 113 projects axially forward from a partial ring 34, to which it is integrally joined, into opening 32. The teeth or serrations on finger 113 engage tang 33 as the finger is pushed through the opening 32. Partial ring 34 is in the form of a C and encloses an angle of a little more than 180°. The open mouth of partial ring 34 easily spans tube 1 as well as the inner part of the conical outer surface of first end piece 3. As the partial ring slides axially outwardly along the surface of first end piece 3, it ultimately comes into gripping contact with the end piece 3 and is rendered stationary. In this way, the locking elements of the coupling are secured together and the tube ends thereby joined in a connection which resists axial disconnection. In order to disconnect the tube ends, the finger 113 is pressed laterally to disengage the tang 33 from engagement with the serrations on finger 113. Partial ring 34 can then be slid inwardly until the finger is out of opening 32. The first and second pieces 3 and 6 can then be separated.

Figure 9:
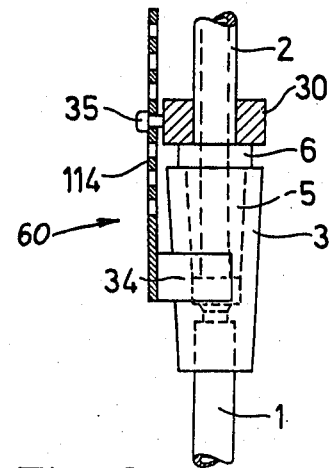
FIG. 9 is similar to FIG. 7 except that the finger is in the form of a perforated tape, the holes of which are adapted to receive a pin to thereby lock the coupling together.

Still another embodiment of the invention is illustrated by FIG. 9. As shown in that figure, the ring 30 has a protruding pin with a head on the end. Finger 114 is in the form of a perforated tape having one end connected to the partial ring 34. The finger 114 has numerous holes, one after the other, in the longitudinal direction. After the partial ring 34 is slid into position on the first end piece 3, the hole in finger 114 lying in front of pin 35 is engaged with the pin to lock the coupling together. The coupling is unlocked by taking the finger 114 off of pin 35.

All of the couplings described above can be made of polymeric materials such as nylon, polystyrene, polypropylene, polyvinyl chloride and synthetic rubber. Rigid and/or flexible or elastomeric polymeric materials can be used as is considered appropriate.

The foregoing detailed description has been given for clearness of understanding only and no unnecessary limitations should be understood therefrom, as modifications will be obvious to those skilled in the art.

What is claimed is:

1. A medical apparatus coupling, for connecting the ends of two tubes, comprising:
   a first end piece for receiving a first tube end, with said first end piece having a conical outer surface and with the end piece being narrower at the end to which the first tube end is joined;
   a second end piece having a first end, and a second end for receiving a second tube end;
   a male conical member on the second end piece and a female conical bore on the first end piece;
   a plurality of fingers, means connecting the fingers to a ring constituting a mounting on and around the second end piece, means securing the ring against axial movement toward the first end of the second end piece with said fingers extending axially along the outside of the first end piece; and
   an axially slidable ring circumscribing the ring containing the fingers, so that sliding of the slidable ring over and along the fingers presses the fingers radially inwardly towards the first end piece when the two end pieces are in coupled arrangement thereby locking the fingers to the first end piece conical outer surface and against radial outer displacement to secure the two end pieces against separation when tension is applied to the end pieces when joined into operative coupled arrangement.

2. A coupling according to claim 1 in which the fingers have smooth surfaces in contact with the ring.

3. A coupling according to claim 1 in which the fingers have serrations on the surfaces in contact with the ring.

4. A coupling according to claim 1 in which the ends of the fingers have means at the end which engage the end of the first end piece to which a tube can be connected.

5. A medical apparatus coupling, for connecting the ends of two tubes, comprising:
- a first end piece for receiving a first tube end, with said first end piece having a conical outer surface and with the end piece being narrower at the end to which the first tube end is joined;
- a second end piece having a first end, and a second end for receiving a second tube end;
- a male conical member on the second end piece and a female conical bore on the first end piece;
- two oppositely positioned fingers, means joining the fingers to a mounting on the second end piece, means securing the mounting against axial movement toward the first end of the second end piece, with said fingers extending axially along the outside of the first end piece; and
- means at the ends of the fingers which is adapted to circumscribe and clamp the fingers to and around the first end piece when the two end pieces are in coupled arrangement, with said means including a locking element on each finger and each locking element having serrations adapted to interlock with serrations on the other locking element thereby locking the fingers to the first end piece conical outer surface and against radial outer displacement to secure the two end pieces against separation when tension is applied to the end pieces when joined into operative coupled arrangement.

6. A medical apparatus coupling, for connecting the ends of two tubes, comprising:
- a first end piece for receiving a first tube end, with said first end piece having a conical outer surface and with the end piece being narrower at the end to which the first tube end is joined;
- a second end piece having a first end, and a second end for receiving a second tube end;
- a male conical member on the second end piece and a female conical bore on the first end piece; and
- two oppositely positioned fingers, means joining the fingers to a mounting on the second end piece, means securing the mounting against axial movement toward the first end of the second end piece, with said fingers extending axially along the outside of the first end piece; and
- means at the ends of the fingers which is adapted to circumscribe and clamp the fingers to and around the first end piece when the two end pieces are in coupled arrangement, with said means including at least one pin on one finger and at least one pin receiving hole on the other finger thereby locking the fingers to the first end piece conical outer surface and against radial outer displacement to secure the two end pieces against separation when tension is applied to the end pieces when joined into operative coupled arrangement.

7. A medical apparatus coupling, for connecting the ends of two tubes, comprising:
- a first end piece having a first end, and a second end for receiving a first tube end;
- a second end piece having a first end, and a second end for receiving a second tube end;
- a male conical member on the second end piece, and a female conical bore on the first end piece with said first end piece having a conical outer surface tapered generally in the same direction as the conical bore;
- at least one finger, means joining the finger to a mounting removably secured to the first end piece with said finger extending to locking means on the second end piece and means securing the locking means against axial movement toward the first end of the second piece;
- said mounting being a C-shaped member which is adapted to engage and partially surround the first end member conical outer surface between its ends thereby restricting axial movement of the C-shaped member towards the first end of the first end piece;
- whereby when the two end pieces are in coupled arrangement and the finger engages the locking means, the two end pieces are secured against separation when tension is applied to the end pieces.

8. A mdeical apparatus coupling according to claim 7 in which the locking means on the second end piece includes a ring having a finger receiving hole.

9. A medical apparatus coupling, for connecting the ends of two tubes, comprising:
- a first end piece having a first end, and a second end for receiving a first tube end;
- a second end piece having a first end, and a second end for receiving a second tube end;
- a male conical member on the second end piece and a female conical bore on the first end piece;
- at least one finger, means joining the finger to a mounting removably secured to the first end piece, with said finger extending to locking means on the second end piece;
- means restricting axial movement of the mounting towards the first end of the first end piece;
- the finger having a plurality of holes and the locking means on the second end piece having a peg engageable with one of said holes at any one time;
- means securing the locking means against axial movement toward the first end of the second piece;
- whereby when the two end pieces are in coupled arrangement and the finger engages the locking means, the two end pieces are secured against separation when tension is applied to the end pieces.

10. A medical apparatus coupling according to claim 9 in which the locking means comprises a ring and the peg is on the ring.

* * * * *